US012539236B2

(12) United States Patent
Elden et al.

(10) Patent No.: US 12,539,236 B2
(45) Date of Patent: Feb. 3, 2026

(54) SURGICAL EAR SPECULUMS

(71) Applicant: Alcon Inc., Fribourg (CH)

(72) Inventors: Wesley Hastings Elden, Southlake, TX (US); Jasmine Tandace Ainetchian, Dallas, TX (US)

(73) Assignee: Alcon Inc., Fribourg (CH)

( * ) Notice: Subject to any disclaimer, the term of this patent is extended or adjusted under 35 U.S.C. 154(b) by 203 days.

(21) Appl. No.: 18/582,819

(22) Filed: Feb. 21, 2024

(65) Prior Publication Data

US 2024/0285441 A1 Aug. 29, 2024

Related U.S. Application Data

(60) Provisional application No. 63/486,695, filed on Feb. 24, 2023.

(51) Int. Cl.

*A61F 11/20* (2022.01)
*A61M 29/00* (2006.01)
*A61B 90/00* (2016.01)

(52) U.S. Cl.

CPC ............. *A61F 11/20* (2022.01); *A61M 29/00* (2013.01); *A61B 2090/08021* (2016.02); *A61M 2210/0662* (2013.01)

(58) Field of Classification Search

CPC ........................................ A61F 11/10
See application file for complete search history.

(56) References Cited

U.S. PATENT DOCUMENTS

| | | | |
|---|---|---|---|
| 3,224,437 A | | 12/1965 | Hardgrove |
| 3,374,791 A | | 3/1968 | Thomas |
| 4,441,485 A | | 4/1984 | Reynolds |
| 5,474,532 A | | 12/1995 | Steppe |
| 5,674,277 A | * | 10/1997 | Freitag ...................... A61F 2/07 623/1.13 |
| 5,916,150 A | | 6/1999 | Sillman |
| 6,083,257 A | * | 7/2000 | Taylor ..................... B21F 45/00 623/1.46 |
| 6,155,987 A | | 12/2000 | Scherl |
| 6,527,736 B1 | | 3/2003 | Attinger |
| 9,119,744 B2 | | 9/2015 | Wellen |
| 10,537,472 B2 | | 1/2020 | Brennan |
| 10,555,834 B2 | | 2/2020 | Charles |
| 10,667,953 B2 | | 6/2020 | Hendricks |

(Continued)

FOREIGN PATENT DOCUMENTS

KR 20200014598 A 2/2020

*Primary Examiner* — Tessa M Matthews

(57) ABSTRACT

Certain embodiments described herein provide a surgical ear speculum comprising a tubular body having an anterior end, a posterior end, and a first length from the anterior end to the posterior end. The tubular body has an inner layer, an outer layer, and a middle layer between the inner layer and the outer layer. The inner layer, the outer layer, and the middle layer are peripherally disposed around a central cavity of the surgical ear speculum. The central cavity extends from the anterior end of the surgical ear speculum to the posterior end of the surgical ear speculum. The inner layer comprises a first membrane, and the outer layer comprises a second membrane. The middle layer comprises an expandable and contractible wire mesh disposed between the first membrane and the second membrane.

15 Claims, 4 Drawing Sheets

(56) References Cited

U.S. PATENT DOCUMENTS

| | | | |
|---|---|---|---|
| 11,020,271 B2 | 6/2021 | Valencia | |
| 11,717,439 B2 | 8/2023 | Maschio | |
| 2003/0097174 A1* | 5/2003 | Henderson | A61F 2/07 623/1.13 |
| 2012/0255564 A1* | 10/2012 | Park | A61F 11/10 128/864 |
| 2014/0194891 A1 | 7/2014 | Shahoian | |
| 2016/0113715 A1 | 4/2016 | Dockett | |
| 2022/0175484 A1 | 6/2022 | Brennan | |
| 2022/0400939 A1 | 12/2022 | Rastani | |
| 2023/0058540 A1 | 2/2023 | Charles | |

* cited by examiner

SURGICAL EAR SPECULUMS

BACKGROUND

Many different diseases and conditions of the ear affect people all over the world. Various otological procedures have been developed to diagnose and treat ear disease. Often the procedures require inserting instruments, such as an endoscope or surgical tools, into the ear. Preparation, sterilization, and treatment of the ear must all be precise to successfully diagnose and treat a condition without damage or infection to the ear.

Such otological procedures may be potentially complicated by presence of debris, such as wax, hair, or blood, in the ear canal that can obstruct clear passage for surgical instruments or cause poor endoscopic vision. Current otological surgery techniques use a cutting tool and vacuum in an attempt to create a clear entry path for surgical instruments and prevent physical or visual obstruction. However, preparing the ear in such a way with a vacuum and a cutting tool is time consuming, tedious, and carries the risk of human error causing trauma to the ear during the vacuuming and cutting.

Further, ear canals may have a natural curvature and shape that varies by person and are typically at-risk for trauma during otological procedures. Therefore, even if the ear is properly prepared using a vacuum and cutting tool, the ear canal is exposed and carries a risk of being damaged during certain otological surgical procedures, especially if the canal is not straight. For example, bone drilling carries a risk of causing damage to the interior surface of the ear canal.

Thus, there is a need in the art for improved tools to assist in otological procedures that address at least some of the issues described above.

BRIEF SUMMARY

The present disclosure relates generally to speculums used in otological procedures, and to methods of using such speculums.

Certain embodiments described herein provide a surgical ear speculum comprising a tubular body having an anterior end, a posterior end, and a first length from the anterior end to the posterior end. The tubular body has an inner layer, an outer layer, and a middle layer between the inner layer and the outer layer. The inner layer, the outer layer, and the middle layer are peripherally disposed around a central cavity of the surgical ear speculum. The central cavity extends from the anterior end of the surgical ear speculum to the posterior end of the surgical ear speculum. The inner layer comprises a first membrane, and the outer layer comprises a second membrane. The middle layer comprises an expandable and contractible wire mesh disposed between the first membrane and the second membrane. When the surgical ear speculum is in a contracted state, the surgical ear speculum at least partially has a first diameter. When the surgical ear speculum is in an expanded state, the surgical ear speculum at least partially has a second diameter greater than the first diameter.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

The present disclosure relates generally to speculums used in otological procedures, and to systems involving and methods of using such speculums.

In certain embodiments, surgical ear speculums as disclosed herein include a tubular body extending a first length from an anterior end of the speculum to a posterior end of the speculum. The body comprises an inner membrane layer, an outer membrane layer, and a structural wire mesh middle layer between the inner and outer layers. When the speculum is placed into an ear canal, it may be expanded such that it exerts a small amount of pressure on the wall of the ear canal to help straighten the canal. The central cavity of the speculum provides a clear pathway for surgical tools, and the membrane layers provide protection, heat-resistance, and/or watertight sealing.

Figure 1:
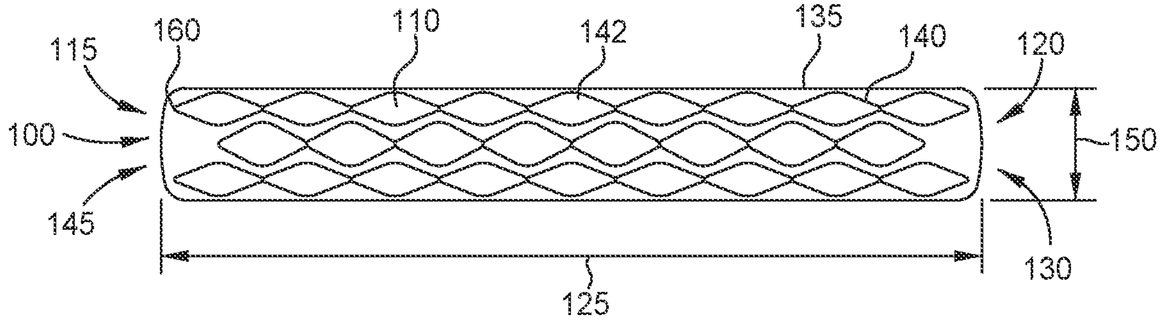
FIG. 1 illustrates a side view of a surgical ear speculum, according to certain embodiments.

FIG. 1 illustrates a side view of a surgical ear speculum 100, according to certain embodiments. As shown, the speculum 100 comprises a tubular body 110 having an anterior end 115, a posterior end 120, and a first length 125 from the anterior end 115 to the posterior end 120. The tubular body 110 includes an inner peripheral layer 130, an outer peripheral layer 135, and a middle peripheral layer 140. The layers 130, 135, 140 are disposed around a central cavity 145 of the speculum 100. When the speculum 100 is placed inside an ear, the central cavity 145 provides clear passage for surgical tools into the ear.

In some embodiments, the inner layer 130 comprises an internally-facing heat resistant or protective membrane (e.g., made of plastic such as silicone or a coated plastic/metal). The outer layer 135 comprises an externally facing waterproof membrane (e.g., made of plastic such as silicone or a coated plastic/metal), and the middle layer 140 comprises a wire mesh 142 that may be contracted for insertion into an ear and expanded once inside the ear. In some embodiments, the mesh 142 may be expanded inside an auditory ear canal so that the speculum 100 exerts sufficient pressure to straighten curved portions of the canal. The length 125 of the speculum 100 may correspond to a length of an ear canal to protect the portion of the ear canal into which the speculum 100 has been inserted from heat or abrasion during surgical procedures, and to provide clear passage for surgical tools into the ear. In some embodiments, the wire mesh 142 may be made of thin stainless steel or another appropriate material (e.g., Nitinol) that allows contraction/expansion of the wire mesh structure.

In some embodiments, the length 125 and diameter 150 of the speculum 100 are selected to be suitable for the length and diameter of an average adult ear canal (about 2.5 cm and 0.7 cm, respectively), average child ear canal, average adolescent ear canal, average female ear canal, average male ear canal, etc. For example, in some embodiments, the length of the speculum 100 may be approximately in a range of 0.5 centimeters (cm) to 4.5 cm. For example, the length of the speculum 100 may be approximately 2.5 cm. Other lengths of the speculum 100 are also contemplated. In some embodiments, the length of the speculum 100 may be longer or shorter than the ear canal. For example, the length of the speculum 100 may be slightly longer than the length of the ear canal to facilitate gripping and removal of the speculum 100. The length of the speculum 100 may also be longer than the ear canal to provide access that extends out of the ear. For example, in some embodiments, the length of the speculum 100 may be approximately in a range of 1 cm to 8 cm. For example, the length of the speculum 100 may be approximately 3.5 cm. Other lengths of the speculum 100 are also contemplated.

In some embodiments, the expanded diameter 150 of the speculum 100 may be slightly greater than a maximum inner diameter of the ear canal to facilitate exertion of pressure on the inner wall of the ear canal. The maximum inner diameter of an ear canal refers to the inner diameter of a portion of the ear canal that is the largest in comparison to the inner diameters of various other portions of the ear canal. Note that the inner diameter of an inner canal may change depending on the shape of the ear canal.

In embodiments where the expanded diameter 150 of the speculum 100 is larger than the diameter of the ear canal, when the speculum 100 is inserted into an ear in a contracted state and then expanded, the speculum 100 will straighten the ear canal and match the shape and diameter of the straightened ear canal along the length of speculum 100. As such, the speculum 100 need not necessarily fully expand along its entire length when in use in a patient's ear canal. Rather, when in use and expanded, the speculum 100 may have a shape matching the shape of the ear canal into which it has been placed, such that at various segments along its length, the speculum 100 may have a diameter between the fully contracted diameter 152 and the fully expanded diameter 150.

In situations where it may be desirable to have more pressure exerted on the inner wall of the ear canal, the expanded diameter 150 may be increased so long as it does not damage the ear canal or cause discomfort to the patient. Regardless, it will be further apparent that the selected length and diameter may be greater or smaller, such as for a person with a very large ear canal or for a child or infant.

In some embodiments, a set of speculums 100 may be provided. The speculums 100 may have different lengths and diameters suitable for various ear shapes and sizes. The set of speculums 100 may each be sterilized, placed in sealed packaging, and discarded after use, eliminating the need for sterilization.

The inner layer 130 may be made from various suitable materials (e.g., plastics and plastic films) having sufficient elasticity to stretch and compress as the speculum 100 expands and contracts while still providing heat resistance or protection from abrasion. The outer layer 135 may be chosen from various suitable materials having sufficient elasticity to stretch and compress as the speculum 100 expands and contracts while still providing a watertight seal. In various embodiments, the speculum 100 may include additional membrane layers. In some embodiments, one or more of the membrane layers 130, 135 may be omitted.

The wire mesh 142 of the middle layer 140 is expandable and contractible. When the mesh 142 is contracted, the speculum 100 has a compressed diameter 152 smaller than the diameter of the ear canal and may be easily inserted therein. The mesh 142 can be expanded to a diameter greater than the diameter of the ear canal, such that when the speculum 100 is inserted into an ear and expanded, the speculum 100 may match a diameter of the ear canal such that the outer layer 135 exerts pressure on the inner wall of the auditory canal.

In some embodiments, the outer layer 135 being pressed against the wall of the ear canal forms a watertight seal around at least a portion of the central cavity 145 of the speculum 100. The watertight seal may facilitate creating an aqueous environment in the central cavity 145, which may be beneficial for performing certain surgical procedures involving the presence of liquids in the ear canal. For example, the presence of liquid during cutting or drilling may lubricate the blade and increase efficiency and accuracy of the cutting or drilling process.

Figure 2:
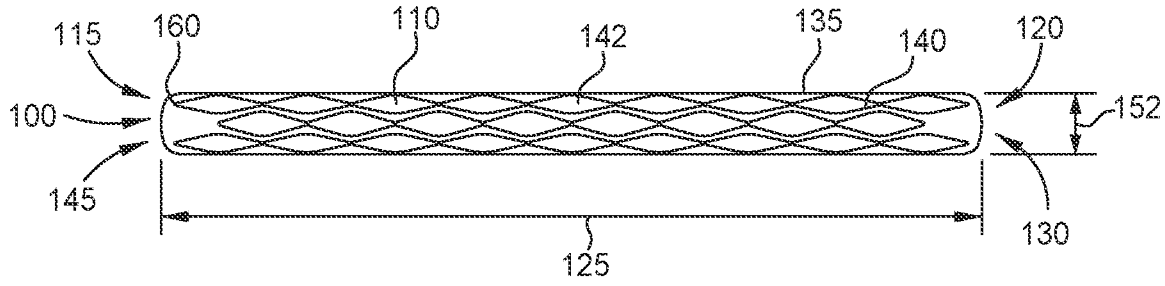
FIG. 2 illustrates a side view of a surgical ear speculum in a compressed state, according to certain embodiments.

FIG. 2 illustrates a side view of a surgical ear speculum 100 in a compressed state, according to certain embodiments. As shown, the speculum 100 comprises a tubular body 110 having an anterior end 115, a posterior end 120, and a first length 125 from the anterior end 115 to the posterior end 120. The tubular body includes an inner peripheral layer 130, an outer peripheral layer 135, and a middle peripheral layer 140. The layers 130, 135, 140 are disposed around a central cavity 145 of the speculum 100.

As shown, the speculum 100 when in a compressed state, has a compressed diameter 152. In certain embodiments, the compressed diameter 152 may be smaller than a minimal diameter of an ear into which the speculum 100 is inserted, thus allowing for easy insertion. As previously mentioned, the speculum 100 may be expanded after insertion into an ear. For example, if an expected diameter of the ear canal is 0.6 cm, the compressed diameter may be approximately in a range of 0.2 to 0.65 cm (other compressed diameters are also contemplated (especially for use with other ear canal diameters)). In some embodiments, the expanded diameter may be approximately the same as or larger than the diameter of the ear canal. For example, if an expected diameter of the ear canal is 0.6 cm, the expanded diameter may be approximately in a range of 0.5 to 0.85 cm (other compressed diameters are also contemplated (especially for use with other ear canal diameters)).

The speculum 100 can be expanded and contracted by relative expansion and contraction of the wire mesh 142. In some embodiments, the wire mesh 142 is expanded (e.g., lengthwise and/or diameter wise) as a result of a user (e.g., surgeon) twisting a portion of the wire mesh 142 that is located near the anterior end 115 in a first direction, e.g., clockwise, and the wire mesh 142 is contracted (e.g., lengthwise and/or diameter wise) by twisting the portion of the wire mesh 142 in a second direction, e.g., counter-clockwise. In other embodiments, the directions of rotation for expansion and contraction may be reversed, i.e., counter-clockwise for expansion, and clockwise for contraction. In some embodiments, the wire mesh 142 may be expanded by compressing the wire mesh 142 (e.g., through a user pushing the wire mesh against a portion of inner ear anatomy). In some embodiments, the wire mesh 142 may be compressed by stretching the wire mesh 142 (e.g., by pulling on ends of the wire mesh 142).

In various embodiments, the speculum 100 may be expanded or contracted by any suitable means, so long as the speculum can be contracted and then easily expanded while in the ear. For example, by locating an expansion/contraction feature at the anterior end 115, the feature may be accessible even while the speculum 100 is inserted into an ear. In some embodiments, such a feature may be included at either the anterior end 115, the posterior end 120, or both ends, such that either end 115, 120, of the speculum 100 may be inserted into the ear.

Figure 3:
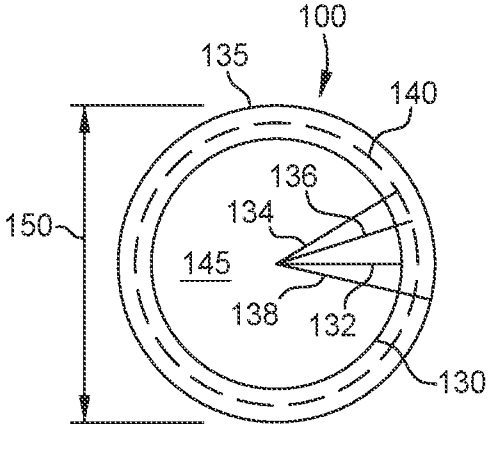
FIG. 3 illustrates a first end view of a surgical ear speculum, according to certain embodiments.

FIG. 3 illustrates a first end view of a surgical ear speculum 100, according to certain embodiments. As shown, the inner layer 130 extends peripherally around the central cavity 145 and has a thickness from a first radius 132 to a second radius 134, the middle layer 140 extends peripherally around the inner layer 130 and the central cavity 145 and has a thickness from the second radius 134 to a third radius 136, and the outer layer 135 extends peripherally around the middle layer 140, the inner layer 130, and the central cavity 145 and has thickness from the third radius 136 to an outer, fourth radius 138.

As previously mentioned, the fully expanded diameter 150 of the speculum 100 may be selected to be the same as or close to a maximum inner diameter of an ear canal, or larger, such that the speculum 100 has a snug fit when inserted into the ear canal in a contracted state and then expanded.

Figure 4:
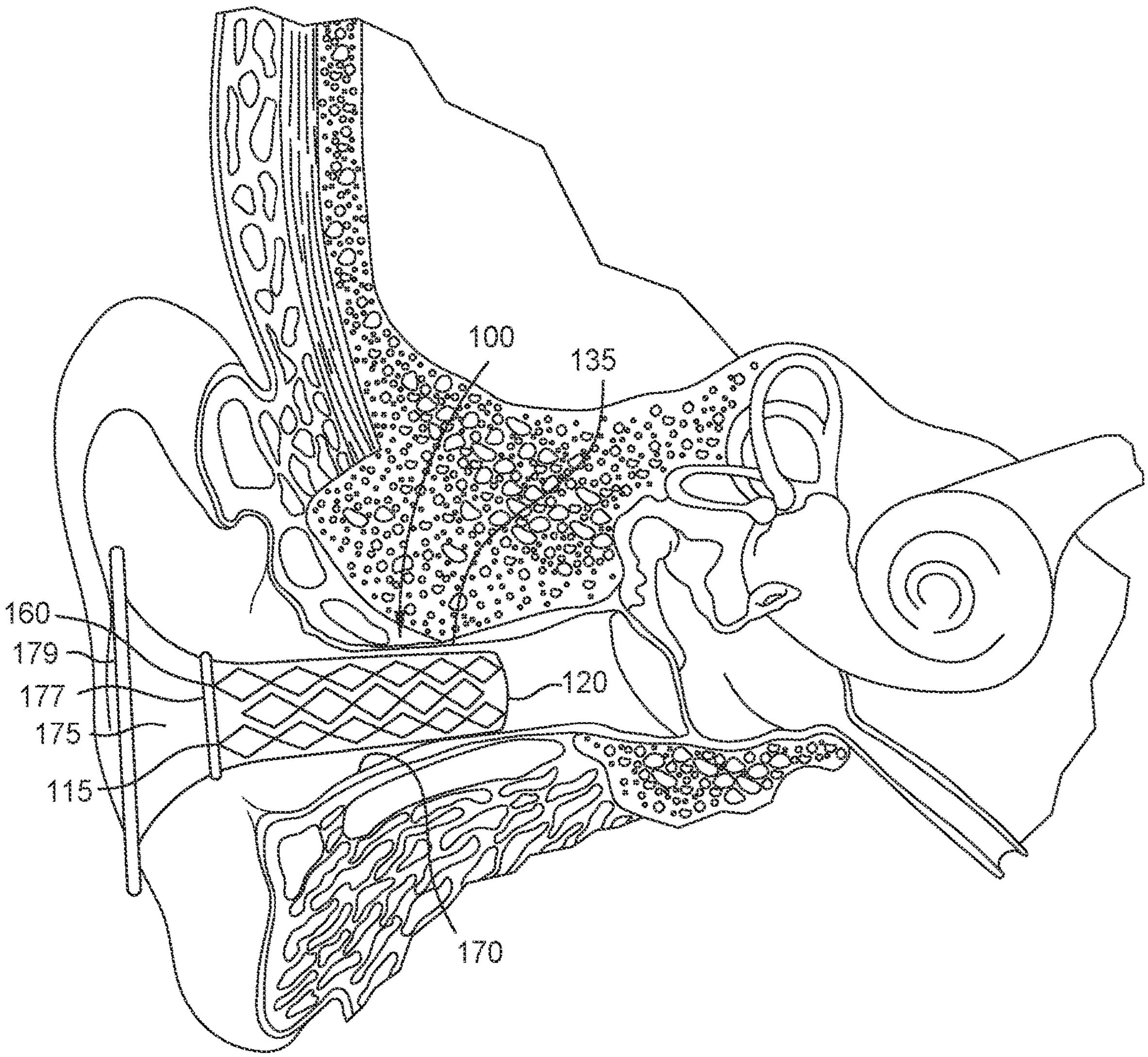
FIG. 4 illustrates a cross-sectional side view of a surgical ear speculum, according to certain embodiments.

FIG. 4 illustrates a cross-sectional side view of a surgical ear speculum 100, according to certain embodiments. As shown, the speculum 100 has been inserted into an ear and expanded such that the outer layer 135 presses against the inner wall 170 of the auditory ear canal. In some embodiments, the speculum 100 at least partially straightens curved portions of the ear canal, such that the central cavity 145 provides a substantially straight, clear pathway into the ear for surgical tools.

In some embodiments, the speculum 100 may include a guiding or control member 175 at the anterior end 115 or posterior end 120 of the speculum 100. For example, a posterior portion 177 of the control member 175 may attach to the anterior end 115 of the speculum 100 and match the diameter 150 or compressed diameter 152 of the speculum 100. The control member 175 may have a tapered shape, with an anterior portion 179 of the control member 175 having a wider diameter than the posterior portion 177. The anterior portion 179 provides an opening or central cavity (e.g., central cavity 145) for instrument insertion. The control member 175 is the portion that can be grasped by the clinician's fingers to navigate the speculum and, therefore, facilitates accurate placement and/or removal of the speculum 100. In some embodiments, the control member 175 interfaces with the wire mesh 142 of the speculum 100 such that the wire mesh 142 may be expanded or contracted by twisting the control member 175 or a portion of the control member 175. For example, the control member 175 may be engaged with the wire mesh 142 such that twisting the control member 175 or a portion of the control member 175 in a first direction, e.g., clockwise, causes the wire mesh 142 to expand and twisting the control member 175 or a portion of the control member 175 in a second direction, e.g., counter-clockwise causes the wire mesh 142 to contract. In some embodiments, the control member 175 may engage with the wire mesh through, for example, a frictional fit or some other mechanical interference mechanism (such as interlocking/complementary mechanical features on the control member 175 and wire mesh 142.

In some embodiments, when the speculum 100 is inserted into an ear with a control member 175 attached, the control member 175 provides a tapered, grippable area 160 which extends out from the anterior end 115 of the speculum 100 and protrudes from a patient's ear to facilitate removal of the speculum 100 from the ear. In some embodiments, the anterior portion 179 of the control member 175 may have a knurled finish to further assist a surgeon in gripping the control member 175.

Figure 5:
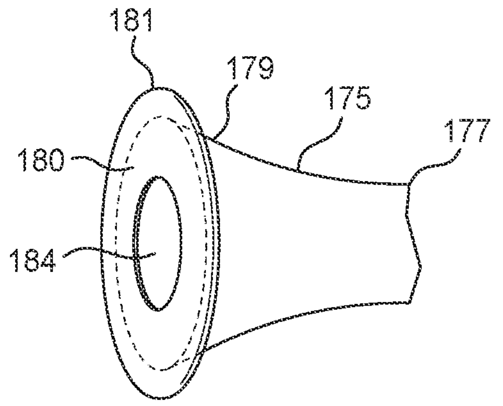
FIG. 5 illustrates a side view of portion of a surgical ear speculum, including a control member and a cap, according to certain embodiments.
Figure 6A:
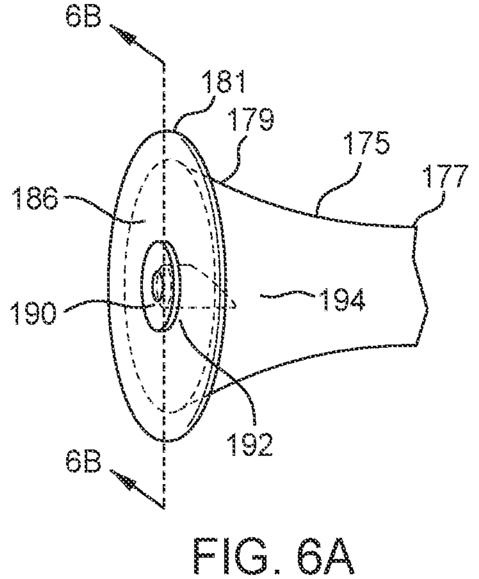
FIG. 6A illustrates a side view of a portion of a surgical ear speculum, including a control member and a solid cap, according to certain embodiments.
Figure 6B:
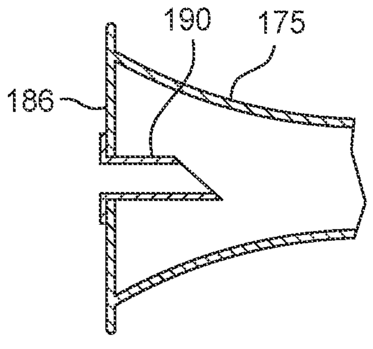
FIG. 6B illustrates a cross-sectional side view of the portion of the surgical ear speculum of FIG. 6A.

In certain embodiments, a cap may be provided within the opening of the control member to prevent fluids or secretions from exiting the ear during surgery. FIGS. 5 and 6A-6B illustrate various examples of control members with different types of caps.

FIG. 5 illustrates a side view of the control member 575 coupled to a cap 580 with a center opening 584, according to certain embodiments. The cap 580 may be fixedly coupled to the control member 575 or may be removable from the control member 575. The cap 580 may be made of a material with suitable stiffness to provide structure without the potential to damage surgical instruments upon entering or exiting the control member 575. In some embodiments, the cap 580 may be made of silicone or a similar material. The cap 580 may be used over the opening 582 of the control member 575 to prevent fluids or secretions from exiting the ear during surgery, beyond the cap 580 of the control member 575.

In some embodiments, the cap 580 may extend only partially across the diameter of the opening 582 of the anterior portion 579 of the control member 575. In some embodiments, the cap 580 may extend inward one quarter of the diameter of the opening 582, such that the center opening 584 of the cap 580 has a diameter of one half of the diameter of opening 582. The center opening 584 may be configured to be large enough to allow surgical instruments to pass through, though small enough to guide the instrument through the tubular body 110.

FIG. 6A illustrates a side view of an example solid cap 686 of another example control member 675, according to certain embodiments. The solid cap 686 may be a circular sheet of material (e.g., silicone) covering the central cavity or opening 687 (e.g., central cavity 145 of FIG. 1) of the anterior portion 679 of the control member 675. In some embodiments, the solid cap 686 may be removable from the control member 675. In other embodiments, the solid cap 686 may be fixedly coupled to the control member 675. The solid cap 686 may be made from a thin and/or pierceable material, such that a cannula 690 may be pressed into and pierce the solid cap 686 to create an opening for an instrument to be inserted while preventing fluids or secretions from exiting the ear during surgery. In some embodiments, the posterior portion 694 of the cannula 690 may be a sharp point to press into and pierce the solid cap 686. In some embodiments, the solid cap 686 may be made of silicone or a similar material.

The length of the cannula 690 may be configured such that, when fully inserted, the cannula 690 extends only a portion of the length of the control member 675. The cannula 690 may have an anterior portion 692 with a lip 696 having a larger diameter than the posterior portion 694. The lip 696 acts as a stop and holds the cannula 690 in position when the posterior portion 694 is fully inserted into the solid cap 686. Providing the solid cap 686 provides the surgeon with the flexibility to place the cannula 690, and therefore the instrument opening, in any suitable location in the opening 687 of the anterior portion 679 of the control member 675. The solid cap 686 may be made of various materials that may be thin enough to allow the cannula 690 to puncture the material.

In some embodiments, the solid cap 686 may not be punctured by the cannula 690 and may instead be punctured by a surgical instrument as the surgical instrument enters the control member 675. In some embodiments, the solid cap 686 may be punctured by a surgical knife. Puncturing the solid cap 686 with a surgical instrument may be more convenient for the surgeon and require fewer components.

FIG. 6B illustrates a cross-sectional view of the solid cap 686 with a cannula 690 coupled to the control member 675 of FIG. 6A. The posterior portion 694 of the cannula 690 extends into the control member 675 and guides the instrument towards the tubular body 110. The cannula 690 may be made of various materials (e.g., plastic, stainless steel, etc.) that allow the cannula 690 to guide the instruments without the potential to damage the instruments.

Figure 7:
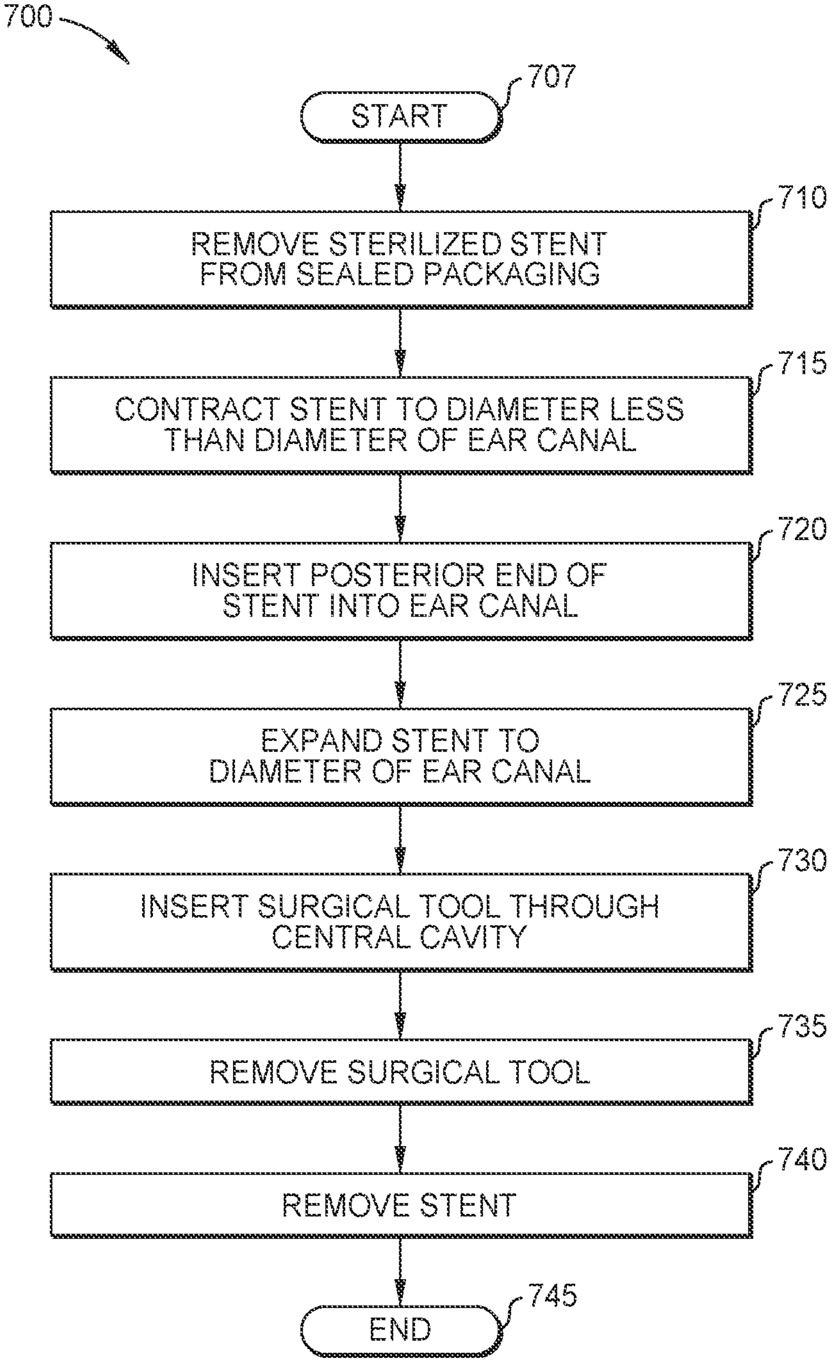
FIG. 7 illustrates a flow chart depicting a method of using a surgical ear speculum, according to certain embodiments.

FIG. 7 illustrates a flow chart depicting a method 700 of using a surgical ear speculum 100, according to certain embodiments. As shown, the method 700 may begin at starting block 705. From starting block 705, the method 700 may proceed to block 710 where a sterilized ear speculum 100 is removed from a sealed packaging. For example, the speculum 100 may be a single use device that comes sterilized in a sealed package and is discarded after use. Although the method 700 is described in relation to a surgical ear speculum 100, the method 700 should not be limited thereto. It will be appreciated that aspects of the method 700 may apply to other similar devices or speculums without departing from the scope of this disclosure.

From block 710 where the ear speculum 100 is removed from the packaging, the method 700 may proceed to block 715 where the speculum 100 is contracted to a diameter less than the diameter of an ear canal into which the speculum 100 is to be inserted. For example, prior to being removed from the packaging, the speculum 100 may have a first diameter equal to or greater than the diameter of an ear canal. A contraction mechanism of the speculum 100 may then be operated to contract the speculum to a diameter that is smaller than the diameter of the ear canal. The amount of contraction may vary, so long as there is adequate clearance for the speculum 100 to be easily inserted without significant friction from the ear canal wall. In another example, the speculum 100 may be packaged in a contracted state, such that it is immediately ready for ear canal insertion after being removed from the packaging. In some embodiments, a tapered control member 175 may be attached to the anterior end 115 of the speculum 100 prior to insertion of the speculum 100 into the ear. The tapered control member 175 may prevent over insertion and facilitate later removal of the speculum 100.

From block 715 where the speculum 100 is contracted, the method 700 may proceed to block 720 where the posterior end 120 of the speculum 100 is inserted into a patient's ear canal. For example, the posterior end 120 may be inserted the length 125 of the speculum 100, such that the anterior end 115 is disposed proximate to the entrance of the ear canal. In another example, a tapered control member 175 may be attached to the anterior end 115 of the speculum 100, and the tapered control member 175 prevents over-insertion of the speculum 100.

From block 720 where the posterior end 120 of the speculum 100 is inserted into the ear canal, the method 700 may proceed to block 725 where the speculum 100 is expanded to a diameter of the ear canal. For example, the middle layer 142 of the speculum 100 may be configured such as that it may be directly expanded by twisting, pushing, or pulling a portion of the mesh 142.

In various embodiments, the diameter 150 of the speculum 100 in a fully decompressed, expanded state may be larger than the diameter of some or all of a patient's ear canal. When the speculum 100 is expanded in a patient's ear, the outer layer 135 presses against the inner wall 170 of the ear canal, exerting pressure and causing one or more curved portions of the ear canal to straighten.

From block 725 where the speculum is expanded to the diameter of the ear canal, the method 700 may proceed to block 730 where a surgical tool is inserted through the central cavity 145 of the speculum 100. For example, the central cavity 145 may provide a clear path of access into the ear for endoscopes, bone drills, or other surgical tools.

From block 730 where the surgical tool is inserted thought the central cavity, the method 700 may proceed to block 735 where the surgical tool is removed. For example, where the surgical tool is removed after completion of surgery.

From block 735 where the surgical tool is removed, the method 700 may proceed to block 740 where the speculum 100 is removed from the patient's ear. In some embodiments, the speculum 100 may be removed by gripping and pulling the anterior end 115. In other embodiments, the speculum 100 is removed by gripping and pulling a control member 175 that has been attached to the anterior end 115 of the speculum 100. Alternatively, the speculum 100 may be recompressed prior to removal. The speculum 100 and control member 175 may both be single use products and may be discarded after removal.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical ear speculum, comprising:

a tubular body having an anterior end, a posterior end, and a first length from the anterior end to the posterior end, the tubular body comprising:

an inner layer;

an outer layer; and a middle layer between the inner layer and the outer layer, wherein:

the inner layer, the middle layer, and the outer layer are peripherally disposed around a central cavity of the surgical ear speculum extending from the anterior end to the posterior end;

the inner layer comprises a first membrane;

the outer layer comprises a second membrane;

the middle layer comprises an expandable and contractible wire mesh disposed between the first membrane and the second membrane;

when in a contracted state, the surgical ear speculum at least partially has a first diameter; and when in an expanded state, the surgical ear speculum at least partially has a second diameter greater than the first diameter.

2. The surgical ear speculum of claim 1, wherein the first membrane comprises an internally-facing heat-resistant membrane.

3. The surgical ear speculum of claim 2, wherein the internally-facing heat-resistant membrane comprises a flexible heat resistant material.

4. The surgical ear speculum of claim 1, wherein the second membrane comprises an externally-facing waterproof membrane.

5. The surgical ear speculum of claim 1, further comprising a tapered control member, the tapered control member being removably attachable to the anterior end of the surgical ear speculum.

6. The surgical ear speculum of claim 1, wherein the expandable and contractible wire mesh is expanded by being twisted in a first direction and contracted by being twisted in a second direction.

7. The surgical ear speculum of claim 1, wherein the surgical ear speculum is sterile and contained inside a sealed packaging.

8. A method, comprising:

removing a sterilized ear speculum from a sealed packaging, the sterilized ear speculum comprising a tubular body having an anterior end, a posterior end, a first length from the anterior end to the posterior end, an inner peripheral layer, an outer peripheral layer, a middle peripheral layer between the inner peripheral layer and the outer peripheral layer, and a central cavity extending along the first length;

contracting the sterilized ear speculum to be in a contracted state wherein the sterilized ear speculum has a contracted diameter less than a diameter of an external ear canal of a patient's ear;

inserting the posterior end of the sterilized ear speculum in the contracted state into the external ear canal;

expanding the sterilized ear speculum to exert pressure on a wall of the external ear canal, and to provide clear passage for surgical tools;

inserting a surgical tool through the central cavity of the sterilized ear speculum;

removing the surgical tool from the central cavity of the sterilized ear speculum; and removing the sterilized ear speculum from the external ear canal.

9. The method of claim 8, further comprises: inserting a bone drill through the central cavity of the sterilized ear speculum.

10. The method of claim 8, further comprises: introducing liquid into the central cavity of the sterilized ear speculum to create an aqueous surgical environment.

11. The method of claim 8, further comprises: performing, with a surgical instrument inserted through the central cavity of the sterilized ear speculum, an otological procedure that generates heat.

12. The method of claim 8, wherein the middle peripheral layer comprises an expandable wire mesh, and wherein expanding the sterilized ear speculum comprises twisting a portion of the expandable wire mesh that is located at the anterior end of the sterilized ear speculum.

13. A system, comprising:

a sealed packaging;

a sterile surgical ear speculum disposed in the sealed packaging, the sterile surgical ear speculum comprising a tubular body having an anterior end, a posterior end, a first length from the anterior end to the posterior end, an inner peripheral membrane layer, an outer membrane peripheral layer, a middle peripheral mesh layer between the inner peripheral membrane layer and the outer peripheral membrane layer, and a central cavity extending along the first length; and at least one surgical instrument, wherein the at least one surgical instrument is inserted through the central cavity of the sterile surgical ear speculum during a surgical procedure.

14. The system of claim 13, further comprising a tapered control member having an anterior control member end with an anterior diameter greater than a posterior diameter of a posterior control member end, wherein the posterior control member end is removably attachable to the anterior end of the sterile surgical ear speculum.

15. The system of claim 13, wherein the sterile surgical ear speculum is a first ear speculum of a plurality of ear speculums having different lengths and diameters.

* * * * *